US010895571B2

(12) United States Patent
Evers et al.

(10) Patent No.: US 10,895,571 B2
(45) Date of Patent: Jan. 19, 2021

(54) REAGENTS, METHODS AND DEVICES TO PREVENT AGGREGATION IN PARTICLE BASED TESTS FOR THE DETECTION OF MULTIMERIC TARGET MOLECULES

(71) Applicant: Minicare B.V., Eindhoven (NL)

(72) Inventors: Toon Hendrik Evers, Eindhoven (NL); Menno Willem Jose Prins, Eindhoven (NL); Jeroen Hans Nieuwenhuis, Eindhoven (NL)

(73) Assignee: SIEMENS HEALTHINEERS NEDERLAND B.V., The Hague (NL)

( * ) Notice: Subject to any disclaimer, the term of this patent is extended or adjusted under 35 U.S.C. 154(b) by 688 days.

(21) Appl. No.: 14/896,182

(22) PCT Filed: Jun. 5, 2014

(86) PCT No.: PCT/IB2014/061986
§ 371 (c)(1),
(2) Date: Dec. 4, 2015

(87) PCT Pub. No.: WO2014/195899
PCT Pub. Date: Dec. 11, 2014

(65) Prior Publication Data
US 2016/0123965 A1 May 5, 2016

(30) Foreign Application Priority Data
Jun. 6, 2013 (EP) ..................................... 13170722

(51) Int. Cl.
G01N 33/543 (2006.01)
G01N 33/53 (2006.01)

(52) U.S. Cl.
CPC ..... G01N 33/5306 (2013.01); G01N 33/54313 (2013.01); G01N 33/54333 (2013.01); G01N 2446/00 (2013.01)

(58) Field of Classification Search
None
See application file for complete search history.

(56) References Cited

U.S. PATENT DOCUMENTS

| 4,376,110 | A * | 3/1983 | David | G01N 33/576 |
| | | | | 435/5 |
| 9,075,052 | B2 | 7/2015 | Schleipen | |
| 9,494,580 | B2 * | 11/2016 | Handa | C08J 3/12 |
| 2001/0049111 | A1 * | 12/2001 | Windhab | B01J 19/0046 |
| | | | | 435/7.1 |
| 2003/0165993 | A1 * | 9/2003 | Buechler | C07K 16/18 |
| | | | | 435/7.1 |
| 2008/0138842 | A1 * | 6/2008 | Boehringer | G01N 33/54306 |
| | | | | 435/7.94 |
| 2009/0042214 | A1 | 2/2009 | Cooke | |
| 2010/0092996 | A1 | 4/2010 | Verschuren | |
| 2010/0285490 | A1 * | 11/2010 | Dees | G01N 33/54373 |
| | | | | 435/7.1 |
| 2012/0014836 | A1 * | 1/2012 | Dittmer | G01N 33/54326 |
| | | | | 422/69 |
| 2012/0164624 | A1 * | 6/2012 | Natan | C12Q 1/6816 |
| | | | | 435/5 |
| 2014/0295432 | A1 | 10/2014 | Evers | |
| 2015/0177239 | A1 | 6/2015 | Evers | |

FOREIGN PATENT DOCUMENTS

| WO | 2003087822 A2 | 10/2003 |
| WO | 2011036634 A1 | 3/2011 |
| WO | 2013072877 A1 | 5/2013 |

OTHER PUBLICATIONS

Diamandis et al., Immunoassay, Academic Press, Chapter 11, The Avidin-Biotin System, pp. 237-267, 1996. (Year: 1996).*
Bruls et al., Rapid integrated biosensor for multiplexed immunoassays based on actuated magnetic nanoparticles, Lab. Chip, 2009, 9, pp. 3504-3510. (Year: 2009).*
Seradyn, SERA-MAG Streptavidin Magnetic Microparticles, Particle Technology, 1996, pp. 1-7. (Year: 1996).*
Binz, H. Kaspar et al "Designing Repeat Proteins: Well-Expressed, SOluble and Stable Proteins from Combinatorial Libraries of Consensus Ankyrin Repeat Proteins", Journal Molecular Biology, vol. 332, 2003, pp. 489-503.
Ebersbach, Hilmar et al "Affilin-Novel Binding Molecules based on Human y-B-Crystallin, an All Beta Sheet Protein", Science Direct, Journal Molecular Biology, vol. 372, 2007, pp. 172-185.
Grabulovski, Dragan et al "A Novel, Non-Immunogenic Fyn SH3-Derived Binding Protein with Tumor Vascular Targeting Properties", Journal of Biological Chemistry, vol. 282, No. 5, 2007, pp. 3196-3204.
Hey, Thomas et al "Artificial, Non-Antibody Binding Proteins for Pharmaceutical and Industrial Applications", Trends in Biotechnology, vol. 23, No. 10, 2005.
Kimura, Richard H. et al "Engineered Knottin Peptides: A New Class of Agents for Imaging Integrin Expression in Living Subjects", American Association for Cancer Research, vol. 69, No. 6, 2009.

(Continued)

Primary Examiner — Gary Counts
(74) Attorney, Agent, or Firm — McCoy Russell LLP

(57) ABSTRACT

Methods for preventing aggregation of detection particles in a test for detecting a multi-epitope target analyte comprising two or more similar or identical epitopes in a sample and/or for determining the concentration of the multi-epitope target analyte in a sample by applying a first capture entity which can specifically bind to at least one epitope on the multi-epitope analyte and block the at least one epitope from binding to a detection particle. The detection of the multi-epitope target analyte may further include the use of a second capture entity, which can specifically bind to the same or a similar epitope of the multi-epitope target analyte as the first capture entity. The multi-epitope target may be detected through the use of a system comprising a sensor surface and the use of a first capture entity to block the at least one epitope from binding to a detection particle.

17 Claims, 6 Drawing Sheets

(56) References Cited

OTHER PUBLICATIONS

Koide, Akiko et al "Monobodies, Antibody Mimics based on the Scaffold of the Fibronectin Type III Domain", Methods in Molecular Biology, vol. 352, 2007, pp. 95-109.
Nielsen, Peter E. et al "An Introduction to Peptide Nucleic Acid", Current Issues Molecular Biology, vol. 1, No. 2, 1999, pp. 89-104.
Nixon, Andrew E. et al "Engineered Protein Inhibitors of Proteases", Current Opinion in Drug Discovery & Development, vol. 9. No. 2, 2006.
Nord, Karin et al "Ginding Proteins Selected from COmbinatorial LIbraries of an-Helical Bacterial Receptor Domain", Nature Biotechnology, vol. 15, 1997.
Silverman, Joshua et al "Mutivalent Avimer Proteins Evolved by Exon Shuffling of a Family of HuMan Receptor Domains", Nature Biotechnology, vol. 23, No. 12, 2005.
Skerra, Arne, "Alternative Binding Proteins: Anticalins—Harnessing the Structural Plasticity of the Lipocalin Ligand Pocket to Engineer Novel Binding Activities", FEBS Journal, vol. 275, 2008, pp. 2677-2683.
"Phenotypic Screening of Phylomer Peptide Libraries Derived from Genome Fragments to Identify and Validate New Targets and Therapeutics" Future Med. Chem. vol. 1, No. 2, 2009, pp. 257-265.
Seydack, Matthias "Nanoparticle Labels in Immunosensing using Optical Detection Methods", Science Direct, Biosensors and Bioelectronics, vol. 20, 2005, pp. 2454-2469.
Wang, Min S. et al "C-Reactive Protein (CRP) Aptamer Binds to Monomeric but not Pentameric Form of CRP", Anal. Bioanal Cem. 2011, vol. 401, pp. 1309-1318.
Luchini, Alessandra et al "Smart Hydrogel Particles: Biomarker Harvesting: One-Step Affinity Purification, Size Exclusion, and Protection against Degradation", Nano Letters, May 2010.
Bruls, D.M. et al "Rapid Integrated Biosensor for Multiplexed Immunoassays based on Actuated Magnetic Nanoparticles", Lab on a Chip, 2009, vol. 9, pp. 3504-3510.

\* cited by examiner

REAGENTS, METHODS AND DEVICES TO PREVENT AGGREGATION IN PARTICLE BASED TESTS FOR THE DETECTION OF MULTIMERIC TARGET MOLECULES

CROSS-REFERENCE TO PRIOR APPLICATIONS

This application is the U.S. National Phase application under 35 U.S.C. § 371 of International Application No. PCT/IB2014/061986, filed on Jun. 5, 2014, which claims the benefit of European Patent Application No. 13170722.6, filed on Jun. 6, 2013. These applications are hereby incorporated by reference herein.

FIELD OF THE INVENTION

The present invention relates to a method for preventing aggregation of detection particles in a test for detecting a multi-epitope target analyte comprising two or more similar or identical epitopes in a sample and/or for determining the concentration of the multi-epitope target analyte in a sample wherein the method comprises the step of applying a first capture entity which can specifically bind to at least one epitope on the multi-epitope analyte, characterized in that the first capture entity blocks the at least one epitope from binding to a detection particle. The invention further relates to a method wherein the detection of the multi-epitope target analyte comprises the use of a second capture entity, which can specifically bind to the same or similar epitope of the multi-epitope target analyte as the first capture entity. Also envisaged is a method for the detection of said multi-epitope target analyte, the performance of the method in a system comprising a sensor surface and the use of a first capture entity to block the at least one epitope from binding to a detection particle such as a magnetic detection particle.

BACKGROUND OF THE INVENTION

The demand for pervasive and effective healthcare moves the world of in vitro diagnostics towards integrated random-access and point-of care solutions. The achievement of such solutions is demanding: the tests needs to be rapid, sensitive, quantitative and accurate. Moreover, the platform on which the test is performed need to be easy to use and compact.

Affinity assays make use of biological molecules to capture specific target molecules from a sample and allow a determination of their concentration. Typically, affinity capture is achieved by dispersing nano- or microparticles coated with capture molecules into sample fluid (Luchini et al., 2008, Nano Lett., 8(1), 350-361). Typical affinity-based assays are therefore used in a huge number of applications such as diagnostic assays, detection of biomolecules in research such as proteins, peptides and nucleic acids thereby making use of affinity molecules such as, e.g. antibodies, which are typically characterized by a high binding affinity towards a specific biomolecule. In principle, the functionalized particles, e.g. magnetic particles, are attracted to a sensor surface, where the particles can indirectly, i.e. by virtue of a captured analyte or directly bind to capture probes such as antibodies printed on the surface. The number of bound particles is directly or inversely related to the amount of target molecules present in the sample. Typically, in such biosensor applications, the particles can be detected using any technique sensitive to a particle close at the surface; often such techniques are based on optical detection such as the detection of scattered light or frustrated total internal reflection (FTIR) as described for instance in Bruls et al., Lab Chip, 2009, 9. 2504-3510.

An important drawback of such affinity-assays as described in the prior art, however, is the fact that in case a target molecule is present in a multimeric form or provides a multitude or similar or identical epitoptes, multiple particles can bind to the same target molecule, which can lead to the formation of bead-target aggregates, i.e. to a clustering. This can drastically reduce the number of particles, e.g. magnetic particles, which can come in close contact with the surface and accordingly may lower the sensitivity of the assay. Moreover, such an aggregation process may occur in a non-reproducible manner, thus leading to inaccurate results of the assay.

There is thus a need to provide means and methods which prevent the clustering of particles in the presence of multimeric or multiepitope target molecules.

OBJECTS AND SUMMARY OF THE INVENTION

The present invention addresses these needs and provides means and methods for preventing the clustering of particles in the presence of multimeric or multiepitope target molecules. The above objective is in particular accomplished by a method for preventing aggregation of detection particles in a test for detecting a multi-epitope target analyte comprising two or more similar or identical epitopes in a sample and/or for determining the concentration of said multi-epitope target analyte in a sample wherein said method comprises the step of applying a first capture entity which can specifically bind to at least one epitope on said multi-epitope analyte, characterized in that said first capture entity blocks the at least one epitope from binding to a detection particle. The employment of such first capture entity leads to a covering of the majority of similar or identical epitopes on the target analyte and leaving only a small portion or single epitopes left. These few epitopes are free and may subsequently or concurrently be bound by a further capture entity which is able to interact with a detection particle. Thereby the otherwise almost unavoidable clustering of detection particles is effectively prevented. This leads to a significant increase of sensitivity of an assay or corresponding detection method and also improves the reproducibility of assays/detection methods, thus increasing the assay/detection method accuracy.

In a preferred embodiment, the detection of said multi-epitope target analyte as mentioned above thus comprises the use of a second capture entity, which can specifically bind to the same or a similar epitope of the multi-epitope target analyte as the first capture entity, wherein the second capture entity comprises a label permitting the binding of the second capture entity to the detection particle.

In yet another preferred embodiment of the present invention the detection of the multi-epitope target analyte comprises the use of a second capture entity, which can specifically bind to the same or a similar epitope of the multi-epitope target analyte as the first capture entity, and wherein the second capture entity is present on the detection particle.

In a further aspect the present invention relates to a method for the detection of a multi-epitope target analyte in a sample and/or for the determination of the concentration of the multi-epitope target analyte in a sample, comprising the steps of:

applying a first capture entity which can specifically bind to at least one epitope on the multi-epitope analyte, characterized in that the first capture entity blocks the at least one epitope from binding to a detection particle;

applying a second capture entity, which can specifically bind to the same epitope of the multi-epitope target analyte as the first capture entity, wherein the second capture entity comprises a label permitting the binding of second capture entity to the detection particle as defined herein above, or wherein the second capture entity is present on the detection particle as defined herein above; and detecting the multi-epitope target analyte with a detection particle capable of binding to the label present on the second capture entity, or with a detection particle comprising a second capture entity which can specifically bind to the epitope of the multi-epitope target analyte, wherein said detection particles are prevented from aggregating.

In a preferred embodiment of the method as defined above, the amount of the first capture entity and/or the amount of the second capture entity to be used in the test is made dependent on (i) the number of detection particles to be used;
(ii) the number of the second capture entity for the multi-epitope target analyte;
(iii) the number of similar or identical epitopes on the multi-epitope target analyte;
(iv) the concentration range of the multi-epitope target analyte to be measured;
(v) the affinity of the first capture entity for the multi-epitope target analyte;
(vi) the affinity of the second capture entity for the multi-epitope target analyte; and/or
(vii) the number of binding sites on the detection particle for the label.

In yet another preferred embodiment of the methods using a first and a second capture entity as defined herein above, the proportion of the first to the second capture entity to be used in the test for detecting a multi-epitope target analyte in a sample and/or for determining the concentration of the multi-epitope target analyte in a sample is n−1 to 1, with n being the number of identical epitopes on the multi-epitope target analyte.

In a further preferred embodiment of the methods the sample comprising the multi-epitope target analyte is contacted with the first and/or the second capture entity before the detection particle is added.

In another preferred embodiment of the present invention the first capture entity and/or the second capture entity is an antibody, antibody fragment such as a Fab fragment, a DNA molecule, an RNA molecule, or a non-immunoglobulin protein.

In a further preferred embodiment, the non-immunoglobulin protein is a designed ankyrin-repeat protein (DARPin), affibody molecule, adnectin, anticalin, affilin, avimer, knottin, fynomer, phylomer or kunitz domain peptide.

In yet another preferred embodiment, the detection of the multi-epitope target analyte in a sample and/or the determination of the concentration of the multi-epitope target analyte in a sample as mentioned above is performed in a system comprising the steps of:

binding the multi-epitope target analyte to the detection particle, contacting the detection particle bound to the multi-epitope target analyte with a sensor surface of the system;

allowing for the binding of a different (non-identical or not similar) epitope of the multi-epitope target analyte by a third capture entity being present on the sensor surface of the system; and detecting the particles remaining at the sensor surface.

In a particularly preferred embodiment, the detection particle is a magnetic particle.

In a further preferred embodiment, the detection of a multi-epitope target analyte in a sample and/or the determination of the concentration of the multi-epitope target analyte in a sample is performed in an optomagnetic system, and the optical detection is in a stationary sample fluid.

In a preferred embodiment, the method as defined herein above additionally comprises the step of magnetically actuating the magnetic particles before detection.

In a further aspect the present invention relates to a use of a first capture entity which can specifically bind to at least one epitope on a multi-epitope analyte comprising two or more similar or identical epitopes for blocking the at least one epitope from binding to a detection particle. It is particularly preferred that the detection particle is a magnetic detection particle.

In a particularly preferred embodiment of the method or use as defined herein above, the multi-epitope analyte is CRP or D-dimer.

DETAILED DESCRIPTION OF THE EMBODIMENTS

Figure 1:
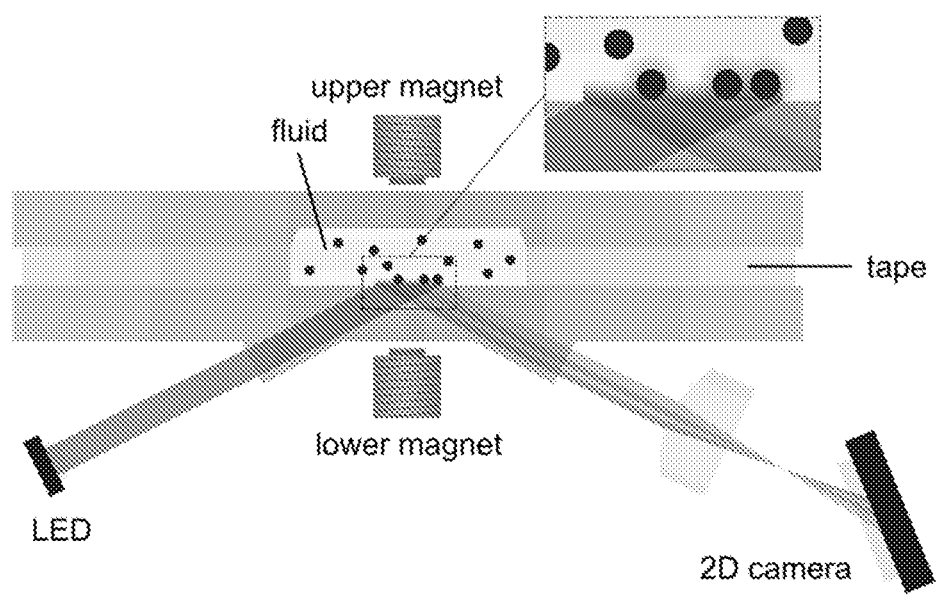
FIG. 1 shows the principle of FTIR detection. Light from a light source enters a cartridge, is reflected from the cartridge/fluid interface and imaged on a detector. If particles are present in the evanescent field, created on this interface, the reflected light intensity decreases.
Figure 2:
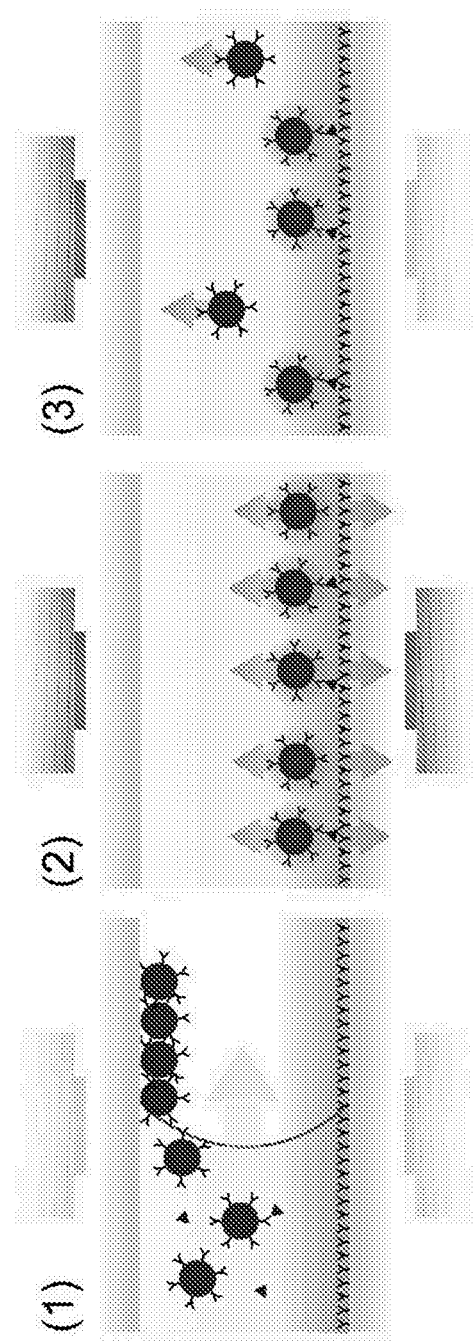
FIG. 2 shows a sandwich immunoassay using Magnotech technology. In panel (1) magnetic particles coated with a primary antibody directed against the target disperse in the sample liquid and bind the target. In panel (2) top and bottom coils actuate the magnetic particles in a pulsed manner, resulting in binding to the sensor surface where a secondary antibody can bind to the bound target molecule. In panel (3) non-bound particles are removed from the sensor surface and bound particles are detected using an evanescent field.
Figure 3:
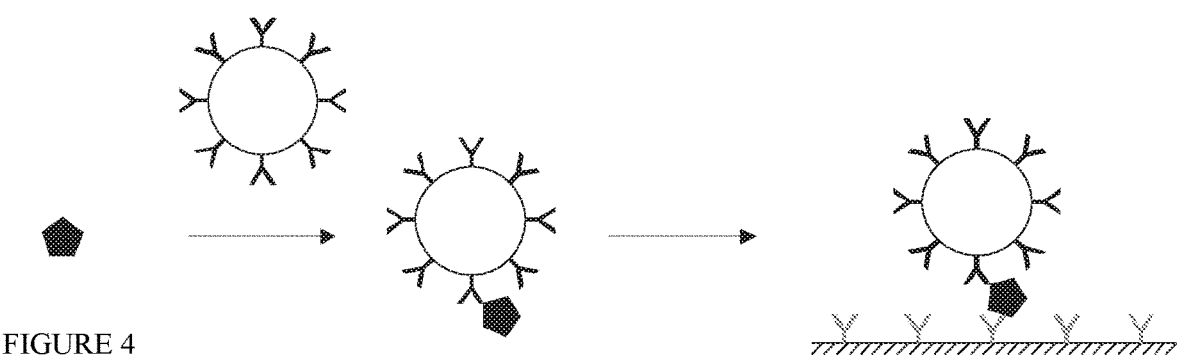
FIG. 3 shows a reaction scheme for magnetic particle sandwich assay. Two different capture molecules (indicated in different shades of grey) can bind to different epitopes on the target molecule.
Figure 4:
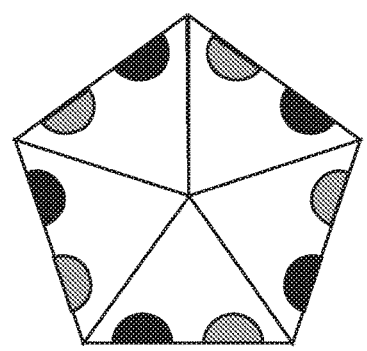
FIG. 4 provides a schematic representation of a pentameric target molecule (e.g. CRP). The black semicircle depicts a binding site for a first capture molecule (coated on the magnetic particle), the grey semicircle represents a binding site for a second capture molecule (coated on the sensor surface).

The present invention relates to means and methods for preventing the clustering of particles in the presence of multimeric or multi-epitope target molecules.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a method for preventing aggregation of detection particles in a test for detecting a multi-epitope target analyte comprising two or more similar or identical epitopes in a sample and/or for determining the concentration of said multi-epitope target analyte in a sample wherein said method comprises the step of applying a first capture entity which can specifically bind to at least one epitope on said multi-epitope analyte, characterized in that said first capture entity blocks the at least one epitope from binding to a detection particle.

The term "detection particle" as used herein means a small, localized object to which can be ascribed a physical property such as volume or mass. In the context of the present invention a detection particle comprises or consists of any suitable material known to the person skilled in the art, e.g. the detection particle may comprise, or consist of, or essentially consist of inorganic or organic material. Typically, a detection particle may comprise, or consist of, or essentially consist of metal or an alloy of metals, or an organic material, or comprise, or consist of, or essentially consist of carbohydrate elements. Examples of envisaged material include agarose, polystyrene, latex, polyvinyl alcohol, silica and ferromagnetic metals, alloys or composition materials. Particularly preferred are magnetic or ferromagnetic metals, alloys or compositions. Particularly preferred detection particles useful in the present invention are superparamagnetic particles. The term "superparamagnetic" as used herein describes a form of magnetism, which appears in small ferromagnetic or ferromagnetic nanoparticles. It is known in the art that in sufficiently small nanoparticles, magnetization can randomly flip direction under the influence of temperature. The time between two flips is referred to as the Néel relaxation time. In the absence of an external magnetic field, when the time used to measure the magnetization of the nanoparticles is much longer than the Neel relaxation time, the magnetization appears to be in average zero, i.e. in the paramagnetic state. In such a state an external magnetic field is able to magnetize the nanoparticles similarly to a paramagnet. However, the magnetic susceptibility is much larger than those of paramagnets.

In specific embodiments of the present invention, the magnetic particle may be an iron containing magnetic particle. In other embodiments, the magnetic particle may include iron oxide such as $Fe_3O_4$, or $Fe_2O_3$, or iron platinum. Also envisaged are alloys with Ni, Co and Cu, or particles comprising these elements. In further embodiments, the magnetic particle may comprise a certain amount of superparamagnetic beads, e.g. 10%, 20%, 30%, 40%, 50%, 60%, 70%, 80%, 90% or more than 90% by weight. Such beads may, for example, comprise en encapsulation with a polymer coating thus providing a bead of a size of around 200 to 300 nm. In preferred embodiments, the material comprised in the magnetic particle may have a saturated moment per volume as high as possible thus allowing to maximize gradient related forces.

In further preferred embodiments, the particle material may have specific properties. The material may, for example, be hydrophobic, or hydrophilic. In further specific embodiments the particle is a plastic particle. Examples of plastic detection particles include latex or polystyrene beads, e.g. those commonly used for purification. In yet another embodiment, the particle may be a cell like detection particle, e.g. having a biological or semi-biological structure, which is present in biological systems or having the form and/or function of biological systems or parts of biological systems.

Furthermore, a detection particle may essentially behave as a whole unit in terms of its transport and properties. Particles may accordingly be of a symmetrical, globular, essentially globular or spherical shape, or be of an irregular, asymmetric shape or form.

The size of a detection particle envisaged by the present invention may ranges between 50 nm and 50 μm. Preferred are detection particles in the nanometer and micrometer range up to several micrometers. In further preferred embodiments the detection particle diameter is larger than 100 nm. The term "diameter" as used herein refers to any straight line segment that passes through the center of the particle and whose endpoints are on the detection particle surface. In case of non-spherical or semi spherical detection particles, the diameter is understood as the average diameter of the largest and shortest straight line segments that pass thought the center of the particle and whose endpoints are on the detection particle surface. Particularly preferred are detection nanoparticles, e.g. detection particles of a diameter of about 100 nm to 10 micrometer, more preferably 100 nm to 3 µm, even more preferably 300 nm to 1000 nm, e.g. 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 620 nm, 650 nm, 670 nm, 700 nm, 720 nm, 750 nm, 770 nm, 800 nm, 820 nm, 850 nm, 870 nm, 900 nm, 920 nm, 950 nm, 970 nm, 1000 nm, or any value in between. Even more preferred are detection nanoparticles having a diameter of about 500 nm. In a particularly preferred embodiment, the material of the detection particle is a magnetic material. In further particularly preferred embodiments, detection particle is a magnetic nanoparticle. In particularly preferred embodiments of the present invention, the material, or particle, e.g. nanoparticle may be superparamagnetic detection particles, which may, for example, be dispersed in an aqueous solution.

In preferred embodiments, the detection particles may comprise on its surface entities which allow, directly or indirectly, to detect the target analyte as defined herein. For example, the detection particle may comprise one or more capture or binding entities, which are capable of specifically binding to a target analyte as defined herein. Also envisaged is the possibility that the detection particle comprises one or more binding entities which are capable or indirectly binding to a target analyte as defined herein, e.g. via further interactors or intermediate linking molecules etc. Such additional binding entities on the detection particle may be understood as third capture entities within the context of the present invention, which are further defined herein below. In certain embodiments, the detection particle may comprise a coating of capture entities, e.g. third capture entities, e.g. a coating of antibodies or antibody fragments or of similar binding molecules, preferably of such elements as define herein below in detail. In specific embodiments, the detection particle may be coated with or covered by an avidin or streptavidin interactor, or by a biotin interactor. Such molecules may accordingly allow the interaction with biotin or avidin molecules, which might be present on the target analyte, e.g. via the previous binding of a biotin or avidin labeled antibody or any other biotin or avidin labeled capture entity. Further preferred examples of interaction couples useful as interactor molecules are biotin/avidin, any antibody/antigen couple, e. g. anti FITC, FITC, anti-Texas-Red/TexasRed, anti-digoxygenin/digoxygenin, and nucleic acid complementary strands. The use of nucleic acid complementary strands is advantageous due to the high degree of multiplexing and the almost unlimited specific combinations. Further envisaged are any suitable interaction couples known to the skilled person.

Figure 5:
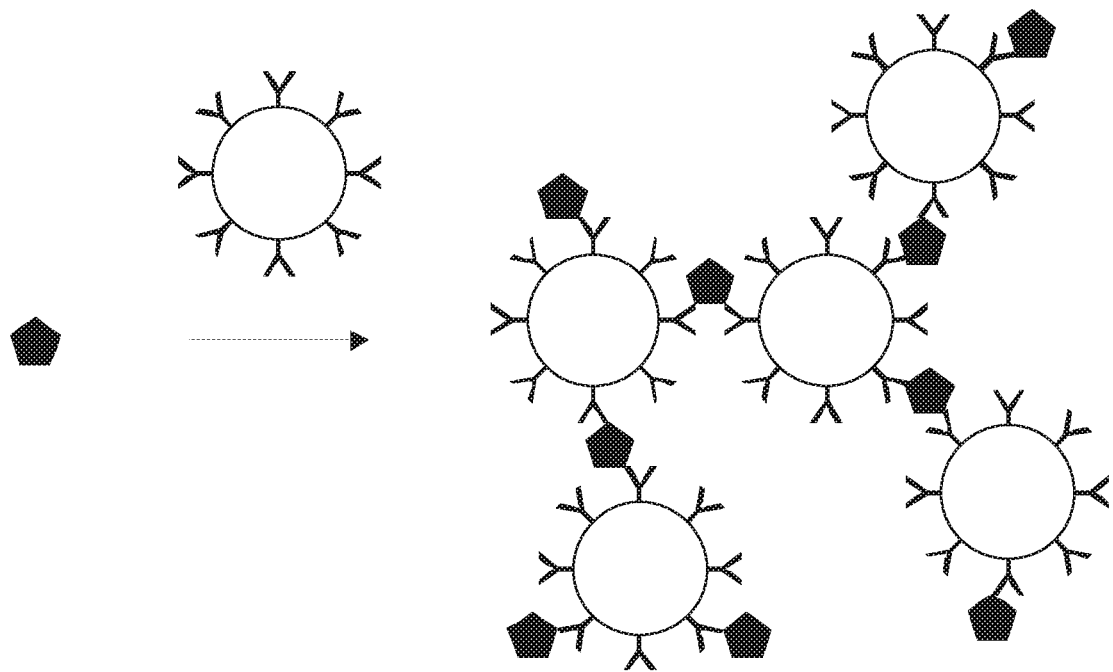
FIG. 5 shows a schematic representation of the clustering process, caused by the presence of multiple binding sites for the capture molecule on the magnetic particles on the same target molecule/complex

The term "aggregation" as used in the context of the detection particles means that two or more detection particles become interconnected and form an aggregate of particles, which prevents free movement and dissociation of the participating particles. The aggregation may be a flat or 2 dimensional aggregation where essentially all particles are provides in a single layer or dimension, or it may be 3 dimensional aggregation, where the particles assemble to a block or cluster of particles. The aggregation may, for example, be caused by the presence of multi-epitope target analytes or any other linking entity or binding molecules which is capable of interacting with two or more detection particles at the same time. An illustrative example of an aggregation, which is however not to be construed as limiting, is provided in FIG. 5.

The term "multi-epitope target analyte" as used herein refers to any substance present in a sample which can be detected or measured, e.g. captured and potentially be isolated according to the methods of the present invention, which comprises two or more similar or identical epitopes. The target analyte may accordingly be a biological target such as a cell, e.g. a prokaryotic cell including a bacterial or archaea cell, or a eukaryotic cell including a fungal, plant, animal, mammal, and human cell; a protein, e.g. a receptor, a ligand, a growth factor, an enzyme, a transcription factor or a fragment of any of these; a peptide; a virus; a hormone; a nucleic acid, e.g. a DNA molecule, or an RNA molecule; or any other suitable biological entity known to the person skilled in the art which comprises two or more similar or identical epitopes. In specific embodiments, the target analyte may be a pathogenic bacterium, a gram positive bacterium, or a gram negative bacterium. Examples of bacteria which may be captured as target analytes are *E. coli, Mycobacterium, Shigella, Borrelia, Salmonella, Enterococcus, Staphylococcus, Streptococcus,* or *Pneumococcus.* The target may further be a chemical target analyte such as a small molecule or a drug molecule. In a typical embodiment, the target analyte may be a protein which exists as a dimer e.g. homo-dimer, trimer, or multimer. It may further typically be a protein complex that consists of 2 or more copies of the same protein, or comprise proteins that contain 2 or more repeats of a subunit. Examples of such target analytes are immunoglobulins like IgG, IgM etc., or nucleic acid sequences that contain multiple repeats of the same sequence, etc.

The term "similar or identical epitope" as used herein refers to the presence of antigenic determinants on the target analyte which can be recognized by a first capture entity.

The antigenic determinants or epitopes present on the target analyte may be conformational epitopes or linear epitopes. The conformational epitopes may have a defined 3D-structure or shape on the basis of a tertiary structure of an entity, e.g. of a protein, i.e. comprise different sectors of the primary sequence of a molecule, e.g. protein. A linear epitope may be a continuous protein sequences of a certain length, e.g. between about 8 and 11 amino acids, or between about 13 to 17 amino acids. The antigenic determinants may accordingly further be similar in terms of sequences and/or structure. Similarity in this context means that the epitope is recognizable by the same binding or capture entity as the other epitopes on the analyte, i.e. by the first capture entity as defined herein. In a preferred embodiment, similar epitopes may be recognized by the same antibody, preferably the same monoclonal antibody. Similar epitopes may, for example, be continuous protein sequences of a certain length, e.g. between about 8 and 11 amino acids, or between about 13 to 17 amino acids, wherein 1, 2, or 3 amino acids are exchanged or modified. Identical epitopes may, for example, be continuous protein sequences of a certain length, e.g. between about 8 and 11 amino acids, or between about 13 to 17 amino acids, which show a complete sequence identity. Similar epitopes may further be conformational epitopes having a 3D-structure and/or shape on the basis of a tertiary structure which shows a highly similarity to the 3D-structure and/or shape of a further epitope, e.g. more than 85%, 90%, or 95% of similarity to the 3D-structure and/or shape of a further epitope. Identical epitopes may be conformational epitopes having a 3D-structure and/or shape on the basis of a tertiary structure which are identical to the 3D-structure and/or shape of a further epitope.

The target analyte may comprise at least more than one of such similar or identical epitope. For example, the analyte may comprise 2, 3, 4, 5, 6, 7, 8, 9, 10, 11, 12, 13, 14, 15, 16, 17, 18, 19, 20, 50, 100, 150 etc. or more of said similar identical epitopes. Thus, all of these epitopes may be recognizable by a first capture entity, e.g. an element of the immune system such as an antibody, or by an entity comprising interacting surfaces or portions of an antibody or an antibody comprising entity or any sub-form or derivative thereof, or by further molecules, which are capable of specifically binding to a molecular structure or epitope as mentioned herein. The target analyte may, in specific embodiments, further comprise similar and identical epitopes, e.g. 2 identical epitopes and 1, 2, 3, 4, 5 etc. epitopes which are similar to said 2 identical epitopes (and also to each other). In addition, the target analyte may comprise one or more additional epitopes, which are not identical or similar to the multi-epitopes as defined above. Accordingly, such secondary epitopes may not be specifically detectable by the first capture entity as defined herein, e.g. by the same antibody or antibody comprising entities, or by entities comprising interacting surfaces or portions of an antibody or by further molecules, which are capable of specifically binding to a molecular structure. Preferably, there is also no cross-reactivity or low specificity-binding between a capture entity capable of binding to the similar or identical epitopes of the target analyte and the secondary non-similar epitope(s) as mentioned above, or between a capture entity capable of binding to the secondary non-similar epitope(s) as mentioned above and the similar or identical epitopes of the target analyte a mentioned above.

The term "first capture entity" as used herein refers to an element of the immune system, e.g. an antibody, or an antibody comprising entity, or an entity comprising interacting surfaces or portions of an antibody, e.g. hypervariable loops which determine the antigen specificity of a given antibody or 1, 2, 3, 4, 5 or 6 CDRs of an antibody or any sub-forms or derivatives thereof, or relates to any further molecule, which is capable of specifically binding to a molecular structure or epitope. The first capture entity may further not be related to immunoglobulin molecules or antibodies, but provide its specific binding capacity by different, alternative mechanisms.

In a preferred embodiment, said first capture entity is an antibody, an antibody fragment, e.g. a Fab fragment, or a nucleic acid or a non-immunoglobulin protein.

An "antibody" as used within the context of the present invention refers to an immunoglobulin molecules and immunologically active portions of immunoglobulin molecules, i.e. molecules that contain an antigen binding site that immunospecifically binds an antigen. The immunoglobulin molecules of the invention can be of any type (e. g., IgG, IgE, IgM, IgD, IgA and IgY), class (e. g., IgG1, IgG2, IgG3, IgG4, IgA1 and IgA2) or subclass of immunoglobulin molecules. Antibodies of the present invention may be described or specified in terms of the epitope(s) or portion(s) of a target molecule, e.g. polypeptide of the present invention, which they recognize or specifically bind. Specific epitopes and their interaction with antibodies would be known to the person skilled in the art. The term "specifically binding" as used herein refers to the immunospecific detection and binding of an antibody to an antigenic epitope. The term "specifically binding" essentially excludes non-specific binding but does not necessarily exclude cross-reactivity with other antigens, in particular with antigens comprising the same antigenic epitope detected by the present antibody. In other words, a cross-reactivity with different epitopes should be excluded, while binding to similar or almost identical epitopes would be envisaged by the specifically binding antibody according to the present invention.

The antibody may be an antibody which specifically binds a target analyte, e.g. a protein structure, a cell or virus surface structure, a chemical molecule or drug, an enzyme or any other target mentioned herein. The antibody may be a polyclonal, monoclonal, multispecific, human, humanized or chimeric antibody, single chain antibody, or constitute a Fab fragment, Fab' fragment, a fragment produced by a Fab expression library, F(ab')2, Fv, disulfide linked Fv, minibody, diabody, scFv, sc(Fv)2, whole immunoglobulin molecule, small modular immunopharmaceutical (SMIP), binding-domain immunoglobulin fusion protein, camelized antibody, $V_{HH}$ containing antibody, an anti-idiotypic (anti-Id) antibody an any epitope-binding fragment(s) of any of the above. Preferred are monoclonal antibodies. The antibodies may further be human antigen-binding antibody fragments and may include Fab, Fab' and F (ab')2, Fv, single-chain Fvs (scFv), sc(Fv)2, single-chain antibodies, disulfide-linked Fvs (sdFv) and fragments comprising either a VL or VH domain.

The antibodies according to the invention may be from any animal origin including birds and mammals. Preferably, the antibodies are human, murine (e.g. mouse and rat), donkey, monkey, rabbit, goat, guinea pig, camel, horse, or chicken antibodies.

The antibodies according to the present invention are preferably monospecific antibodies.

The nucleic acid molecule may for example be DNA or RNA or a PNA, CNA, HNA, LNA or ANA molecule, or any mixture or combination thereof, or any mixture or combination with other lables or eptiopes. The term "PNA" relates to a peptide nucleic acid, i.e. an artificially synthesized polymer similar to DNA or RNA which is used in biological research and medical treatments, but which is not known to occur naturally. The PNA backbone is typically composed of repeating N-(2-aminoethyl)-glycine units linked by peptide bonds. The various purine and pyrimidine bases are linked to the backbone by methylene carbonyl bonds. PNAs are generally depicted like peptides, with the N-terminus at the first (left) position and the C-terminus at the right. While DNA and RNA have a desoxyribose and ribose sugar backbone, respectively, the PNA-backbone is composed of repeating N-(2-aminoethyl)-glycine units linked by peptide bonds. It is known in the art that PNA oligomers also show greater specificity in binding to complementary DNAs. Further details may be derived from any suitable literature source or textbook, e.g. Nielsen P E, Egholm M (1999), An Introduction to Peptide Nucleic Acid, Curr. Issues Mol. Biol. 1 (2): 89-104. The term "CNA" relates to an aminocyclohexylethane acid nucleic acid. Furthermore, the term relates to a cyclopentane nucleic acid, i.e. a nucleic acid molecule comprising for example 2'-deoxycarbaguanosine. The term "HNA" relates to hexitol nucleic acids, i.e. DNA analogues which are built up from standard nucleobases and a phosphorylated 1,5-anhydrohexitol backbone. The term "LNA" relates to locked nucleic acids. Typically, a locked nucleic acid is a modified and thus inaccessible RNA nucleotide.

The ribose moiety of an LNA nucleotide may be modified with an extra bridge connecting the 2' and 4' carbons. Such a bridge locks the ribose in a 3'-endo structural conformation. The locked ribose conformation enhances base stacking and backbone pre-organization. This may significantly increase the thermal stability, i.e. melting temperature of the oligonucleotide. The term "ANA" relates to arabinoic nucleic acids or derivatives thereof. A preferred ANA derivative in the context of the present invention is a 2'-deoxy-2'-fluoro-beta-D-arabinonucleoside (2'F-ANA).

The term "non-immunoglobulin protein" as used herein refers to a group of highly affine proteins which are capable of specifically binding to target molecules such as ribosomal proteins, but do not comprise immunoglobulin domains or elements. The non-immunoglobulin proteins may offer several distinct mechanisms of binding and preferably have a similar affinity for target structures such as ribosomal proteins as defined herein above as antibodies.

Preferred examples of non-immunoglobulin proteins which may be used in the context of the present invention include protein structures comprising ankyrin-repeats. Typically, in designed ankyrin-repeat proteins (DARPins) three, four or preferably five repeat ankyrin motifs are present. These may form a stable protein domain with a large potential target interaction surface. Further details may be derived, for example, from Binz et al., 2003, J. Mol. Biol.; 332(2): 489-503.

A further preferred example of a highly affine non-immunoglobulin protein is an affibody molecule, i.e. a protein based on the Z domain (the immunoglobulin G binding domain) of protein A. In contrast to antibodies, affibody molecules are typically composed of alpha helices and lack disulfide bridges. They may be expressed in soluble and proteolytically stable forms in various host cells. Affibody molecules may further be fused with other proteins. Further details may be derived, for example, from Nord et al., 1997, Nat. Biotechnol.; 15(8): 772-777.

The group of highly affine non-immunoglobulin proteins according to the present invention also comprises adnectins. Adnectins are based on the structure of human fibronectin, in particular its extracellular type III domain, which has a structure similar to antibody variable domains, comprising seven beta sheets forming a barrel and three exposed loops on each side corresponding to the three complementarity determining regions. Adnectins typically lack binding sites for metal ions and central disulfide bonds. They are approximately 15 times smaller than an IgG type antibody and comparable to the size of a single variable domain of an antibody. Adnectins may be customized in order to generate and/or increase specificity for target analytes by modifying the loops between the second and third beta sheets and between the sixth and seventh sheets. Further details may be derived, for example, from Koide and Koide, 2007, Methods Mol. Biol.; 352: 95-109.

A further preferred example is the antibody mimetic anticalin, which is derived from human lipocalin. Anticalins typically have the property of binding protein antigens, as well as small molecule antigens. They are composed of a barrel structure formed by 8 antiparallel beta sheets, connected by loops and an attached alpha helix. Mutagenesis of amino acids at the binding site may allow for changing of affinity and selectivity of the molecule. Further details may be derived, for example, from Skerra, 2008, FEBS J., 275 (11): 2677-83.

Another preferred example is affilin, i.e. a genetically engineered protein with the ability to selectively bind antigens, which is structurally derived from gamma-B crystallin or from ubiquitin. Affilins are typically constructed by modification of near-surface amino acids of gamma-B crystallin or ubiquitin and isolated by display techniques such as phage display. The molecular mass of crystallin and ubiquitin based affilins is typically about one eighth or one sixteenth of an IgG antibody, respectively. This may lead to heat stability up to 90° C. and an improved stability towards acids and bases. Further details may be derived, for example, from Ebersbach et al., 2007 J Mol Biol.; 372(1): 172-185 or from Hey et al., 2005, Trends Biotechnol.; 23(10): 514-522.

The group of highly affine non-immunoglobulin proteins also comprises avimers, i.e. artificial proteins that are able to specifically bind to certain antigens via multiple binding sites. Typically, the individual avimer sequences are derived from A domains of various membrane receptors and have a rigid structure, stabilized by disulfide bonds and calcium. Each A domain can bind to a certain epitope of the target molecule. The combination of domains binding to different epitopes of the same target molecule may increases affinity to this target. Further details may be derived, for example, from Silverman et al., 2005, Nat. Biotechnol.; 23(12): 1556-61.

Further preferred examples include knottins, i.e. small disulfide-rich proteins characterized by a special disulfide through disulfide knot. This knot is typically obtained when one disulfide bridge crosses the macrocycle formed by two other disulfides and the interconnecting backbone (disulfide III-VI goes through disulfides I-IV and II-V). Knottin peptides could be shown to bind with high affinity (about 10 to 30 nmol/L) to integrin receptors. The knottin scaffold may accordingly be used for the design of highly affine molecules which are able to bind detection moieties according to the invention. Further details may be derived, for example, from Kimura et al., 2009, Cancer Res., 69; 2435.

The group of highly affine non-immunoglobulin proteins additionally comprises fynomers, i.e. Fyn SH3-derived proteins .Fyn is a 59-kDa member of the Src family of tyrosine kinases. The Fyn SH3 domain comprises 63 residues, and its amino acid sequence is fully conserved among man, mouse, rat, and monkey. Fynomers are typically composed of two antiparallel beta sheets and contain two flexible loops (RT and n-Src loops) to interact with other proteins or targets. Further details may be derived, for example, from Grabulovski et al., 2007, Journal of Biological Chemistry, 282 (5): 3196-3204.

Yet another preferred example of a highly affine non-immunoglobulin molecule is a phylomer peptide. Phylomer peptides are bioactive fragments of naturally occurring proteins that are encoded in the genomes of evolutionary diverse microbes, which are partially sourced from extreme environments and may have evolved over billions of years, providing a multitude of distinct and stable structures capable of binding to biological molecules. Further details may be derived, for example, from Watt, 2009, Future Med. Chem., 1(2): 257-265.

The group of preferred highly affine non-immunoglobulin molecule also comprises kunitz domain peptides. Kunitz domains are the active domains of Kunitz-type protease inhibitors. They typically have a length of about 50 to 60 amino acids and a molecular weight of 6 kDa. Examples of Kunitz-type protease inhibitors are aprotinin, Alzheimer's amyloid precursor protein (APP), and tissue factor pathway inhibitor (TFPI). Kunitz domains are stable as standalone peptides and are able to recognize specific targets such as protein structure and may accordingly be used for the design of highly affine molecules which are able to bind detection moieties according to the invention. Further details may be derived, for example, from Nixon and Wood, 2006, Curr. Opin. Drug Discov. Devel., 9(2), 261-268.

It is preferred that the first capture entity is a designed ankyrin-repeat protein (DARPin), affibody molecule, adnectin, anticalin, affilin, avimer, knottin, fynomer, phylomer or kunitz domain peptide as described above.

The first capture entity is adapted to block at least one epitope of said multi-epitope target analyte. The blocked epitope is preferably the epitope which is present in similar or identical form in two or more copies on the target analyte. The term "blocking" as used herein means that the epitope is bound to and/or covered by the first capture entity such that the epitope is no longer capable of interacting with a further capture entity. The blocking preferably avoids a binding of capture entities present on a detection particle with a target analyte as defined herein. The present invention, however, also envisages further scenarios, wherein the blocking may not involve a direct interaction with the detection particle.

The blocking may preferably be a partial blocking of similar or identical epitopes on a target analyte. For example, the first capture entity may bind to about 60%, 65%, 70%, 75%, 80%, 85%, 90%, 95%, 96%, 97%, 98%, 99% or any value in between these values, of the similar or identical epitopes present on the target analyte. The remainder of the epitopes may be freely accessible after the blocking step. Also envisaged is a blocking which leads to a complete blocking of all epitopes of a sub-portion of all target analytes in a sample and a partial blocking of the remainder of the target analytes in a sample The blocking may be a permanent blocking or a reversible blocking. Permanent blocking may, for example, include additional fixation steps such as crosslinking or UV treatment. A reversible blocking may be blocking which can be overcome by changing the concentration of the first capture entity, by applying chemicals which influence the binding of the capture entity to the target analyte, or by applying mechanical forces, e.g. by agitating the target analytes.

A "sample" as used herein refers to any sample, which includes a target analyte as defined herein. Such samples may, for example, include bodily fluid samples. For examples the bodily fluid may be derived from or comprise stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, e.g. from all suitable organs, e.g. the lung, the muscle, brain, liver, skin, pancreas, stomach, etc., a nucleated cell sample, a fluid associated with a mucosal surface, hair, or skin. In addition, samples from environmental sources, e.g. water samples, meat or poultry samples, soil samples, samples from sources of potential contamination etc., biological samples, food samples, agricultural sample may be used.

A target molecule may be directly obtained from the sample as described herein above. In other situations samples may be subjected to sample preparation techniques, e.g. based on standard protocols, including, for example, partial purification, which renders the target molecules more accessible to binding partners. For example, blood samples may be centrifuged to separate fractions including whole cells or membranes from serum, feces samples may be sectioned and homogenized with physiologically acceptable buffer and detergent, sputum samples may be liquefied and fractionated. Furthermore, antibiotics or bactericides may be added to samples to prevent further growth of any organisms present. Whole cells may also be removed or may be lysed to release their contents. In other embodiments, the sample may be homogenized and/or resuspended in a suitable buffer solution. Such a homogenization and resuspension in a suitable buffer may also be used in case of non-liquid stool samples, e.g. in solid feces samples. In further embodiments bodily fluid or sample material as mentioned herein above may be processed by adding chemical or biological reactants. This may be performed in order to stabilize the sample material, to remove sample components, or to avoid interaction in samples. For example, EDTA or heparin may be used to stabilize blood samples. It is preferred using blood, i.e. whole blood or blood plasma, or urine or saliva samples.

The "test for detecting a multi-epitope target analyte" in which the aggregation should advantageously be prevented may be any suitable molecular assay or molecular test known to the skilled person. The test may, for example, be an immunoassay, an ELISA assay, an assay comprising optical and/or magnetic elements, a test based on DNA or RNA entities etc. Preferably, the test is an immunological test on the basis of optomagnetic principles. The test may be a qualitative test, e.g. leading to an answer to the question whether the analyte is present in a sample or not, or it may be a quantitative test, e.g. providing an answer to the question of how much of the analyte is present in a sample.

Similarly, the "test for determining the concentration of a multi-epitope target analyte" in which the aggregation should be prevented may be any suitable concentration measurement approach known to the skilled person. Such an approach may be based on a test as described above, e.g. an immunoassay, en ELISA assay, an assay comprising optical and/or magnetic elements, a test based on DNA or RNA entities etc. Preferably, the concentration measurement based on an immunological test on the basis of optomagnetic principles.

In a typical embodiment, the method comprising the step of blocking epitopes is extended by a further step which allows the detection of said multi-epitope analyte as defined herein above. This additional step comprises the employment of a second capture entity. This second capture entity is preferably capable of specifically binding to the same or a similar epitope as the first capture entity defined herein above. The term "second capture entity" as used herein refers—as the first capture entity—to an element of the immune system, e.g. an antibody, or an antibody comprising entity, or an entity comprising interacting surfaces or portions of an antibody, e.g. hypervariable loops which determine the antigen specificity of a given antibody or 1, 2, 3, 4, 5 or 6 CDRs of an antibody or any sub-forms or derivatives thereof, or relates to any further molecule, which is capable of specifically binding to a molecular structure or epitope.

In a preferred embodiment, said second capture entity is an antibody, an antibody fragment, e.g. a Fab fragment. The second capture entity may further not be related to immunoglobulin molecules or antibodies, but provide its specific binding capacity by different, alternative mechanisms. The second capture entity may, for instance be a nucleic acid or a non-immunoglobulin protein, It is preferred that the scone capture entity is an antibody or fragment thereof as defined herein above, or a nucleic acid such as DNA or RNA etc. as defined herein above.

It is further preferred that the second capture entity is non-immunoglobulin protein such as a designed ankyrin-repeat protein (DARPin), affibody molecule, adnectin, anticalin, affilin, avimer, knottin, fynomer, phylomer or a kunitz domain peptide as described herein.

The second capture entity may be functionally and/or structurally identical or similar to the first capture entity, or it may be functionally and/or structurally different from the first capture entity, although providing the same specific binding properties to the multi epitopes of the target analyte as described above.

In preferred embodiments, the second capture entitys may be functionally and/or structurally identical to the first capture entity and additionally comprise a label. The term "label" as used herein refers to a recognizable entity such as an epitope or interactor domain, which allows a specific binding between the label (and the capture entity comprising the label) and a further capture entity. Preferably, the label may be recognizable by a detection particle as defined herein. For example, a capture entity present on said detection particle may be capable of specifically interaction with said label or specifically binding to said label. Thereby, a binding of the target analyte to the detection particle is achievable via the interaction of the second capture entity which may be capable of binding to one of the multiple similar or identical epitopes of the target analyte and which at the same time provides a sector or portion (label) which allows for an interaction or binding to the detection particle. In specific embodiment, the non-labeled capture entity may be, for example, a rabbit antibody or IgG, whereas the labeled capture entity may be a mouse IgG. Both of these capture entities may have an affinity for the same target analyte, i.e. the same epitope of the target analyte as described herein. In this scenario the detection particle may comprise an anti-mouse antibody or IgG, thus being able to specifically bind to the mouse antibody or IgG only. Also envisaged are variants of the described interaction, such as combinations of antibodies or IgGs derived from other organisms etc.

Envisaged examples of suitable labels include avidin, avidin-related proteins, avidin-like entities such as tamavidin 1 and 2, bradavidin, NeutrAvidin, or streptavidin or derivatives or homologues thereof. These proteins typically bind in a specific manner to biotin, e.g. to biotin-comprising structures. In further embodiments, the lable may be biotin, which may interact with avidin, avidin-related proteins, avidin-like entities such as tamavidin 1 and 2, bradavidin, NeutrAvidin, or streptavidin or derivatives or homologues thereof. Further preferred examples of labels are any antigens or epitopes which can be bound by or bind to an antibody or part thereof. Also envisaged are labels such as FITC, which can be recognized by anti-FITC capture molecules, Texas Red, which can recognized by anti-TexasRed molecules, e.g. antibodies or digoxygenin, which can be recognized by anti-digoxygenin molecules, e.g. antibodies. Further envisaged is the use of nucleic acid molecule, preferably single stranded nucleic acid molecules, as labels. These molecules may be recognized by complementary nucleic acid molecules, or by antibodies or any other molecule which is able to specifically recognize the structure or sequence of the nucleic acid molecule. The nucleic acid molecule may accordingly be DNA or RNA or a PNA, CNA, HNA, LNA or ANA molecule, as defined herein above, or any mixture or combination thereof, or any mixture or combination with other labels or epitopes.

Figure 6:
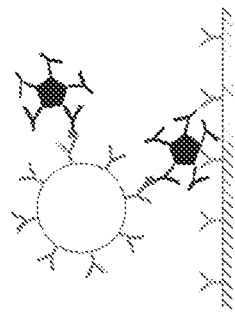
FIG. 6 depicts a reaction scheme, describing a sandwich immunoassay for a multimeric target (black pentamer). The target is reacted with a mixture of capture molecules, of which a portion carries a unique label (square). The formed complex is then reacted with magnetic particles functionalized with capture molecules that can bind to the label. Finally, the magnetic particles with the captured target molecule are brought in contact with the sensor surface, where another capture molecule (light grey) can bind to a different epitope on the target molecule.
Figure 6:
Figure 6:
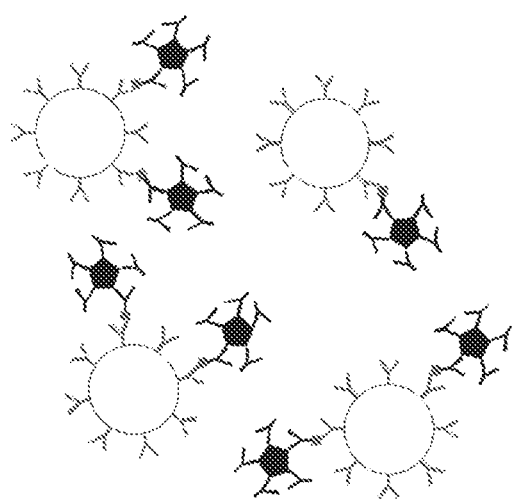
Figure 6:
Figure 6:
Figure 6:
Figure 6:
Figure 7:
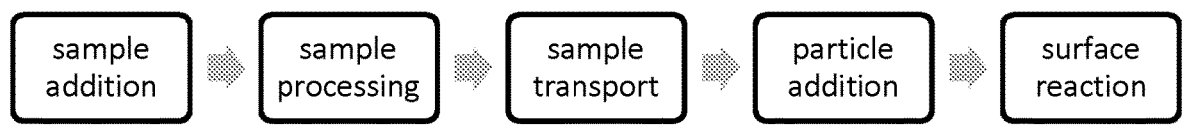
FIG. 7 shows a scheme of different processes taking place for an immunoassay in a disposable cartridge.

In a specific variant of this embodiment, the detection particle as mentioned above may not comprise any capture entity which is capable of directly binding to the target analyte. The detection particle may instead comprise or be covered or coated with a capture entity which is capable of specifically binding to the label as defined herein above. Thereby a clustering of detection particles is prevented while stabilizing the sensitivity of the tests by allowing interaction between the label and its cognate recognition partner. An illustrative example, which is not to be construed as limiting the invention, is provided in FIG. 6.

In further preferred embodiments, the second capture entities may be functionally and/or structurally identical to the first capture entity and be present on a detection particle as defined herein. In this scenario, which resembles the situation depicted in FIG. 5, albeit without the blocking of the first capture entity, use of a label is not required since the interacting partner is provided by the detection particles itself.

A "third capture entity" according to the present invention relates to a capture entity as described herein above, e.g. in the context of the first and second capture entity. The third capture entity is present on the detection particle as defined above and may preferably bind a second capture entity comprising a label. Particularly preferred are interaction couples between the second and third capture entity as defined herein above in the context of the detection particle.

The second capture entity may be used together with the first capture entity such that a suitable proportion or suitable amount of the similar or identical multiple epitopes of the target analyte are blocked by the first capture entity, while a suitable proportion or suitable amount of said multiple epitopes is not blocked by the first capture entity and can thus be recognized and bound by the second capture entity. The "suitable proportion" or "suitable amount" may depend on several features of the elements of the method and can in principle be determined by the skilled person according to pre-tests, calibrations or on the basis of literature knowledge. For example, such pre-tests or calibration approaches may be varying the amount of first capture entity present in the method and for each different amount performing the method with known concentrations of target analyte in the desired range. The amount of first capture entity for which the method displays the best performance, e.g. is most sensitive, may be selected. Alternatively, similar tests with a fixed amount of first capture entity can be used and the amount of second capture entity can be varied. In a further alternative, similar tests can be performed in which the amount of particles can be varied. In yet another alternative, similar tests can be performed where combinations of all of the above parameters are varied and tested. Further details and particulars of such tests would be known to the skilled person or can be derived from suitable literature sources.

Typically, the suitable proportion or amount of the first and/or second capture entity to be used in a test or other application according to the present invention may depend on the number of detection particles to be used in a test. If there are very few detection particles, the likelihood of aggregation may be less pronounced and the test may be prone to insensitivity due to a non-binding of target analytes, e.g. if many binding sites are blocked. Accordingly, in this scenario, the blocking of the multiple similar or identical epitopes via the first capture entity should lead to a covering of about 60 to 80% of the available multiple similar or identical epitopes on one target analyte. This should be balanced with the scenario that there are more detection particles than target analytes in the sample, so that the chance that multiple analytes bind to the same particle decreases. This may lead to a different covering of the similar or identical epitopes on the target analyte. Calculations of suitable proportions and amounts should take into account both situations and may vary in dependence of further factors describe herein, e.g. the envisaged sensitivity etc.

Accordingly, in a specific embodiment the amount of the first capture entity and the amount of the second capture entity to be used in the context of the present invention may be made dependent on the number of detection particles to be used. Thus, first and second capture entity may be made available, in certain embodiments, in a way that essentially all target analytes can be bound at least once by the second capture entity. In further embodiments, it might alternatively be envisaged not to bind a certain fraction of target analytes, i.e. to provide the first capture entity and the second capture entity in such an amount that not all target analytes are bound or covered. This may be used in order to improve the reproducibility of the test should necessity arise, or it may be used to reduce clustering events.

Further, the suitable proportion or amount of the first and/or second capture entity to be used in a test or other application according to the present invention may depend on the number of similar or identical epitopes on a target analyte. The proportion may, for example, be roughly oriented on a stoichiometric calculation of epitopes present on a target analyte. This information may be derivable from suitable literature sources or databases, or it may be determined on the basis or quantitative pre-tests carried out with the target analyte and the capture entity, e.g. under the specific test conditions required. In one example, the suitable proportion may be chosen such that all but a predefined number of epitopes becomes blocked. This may be one epitope, two epitopes, 3, 4, 5, 6, 7, 8, 9, 10 etc. epitopes per target analyte which are not blocked. In certain embodiments, the first and the second capture entity are provided in excess of the number of epitopes on the target molecule multiplied by the assumed maximum number of target molecules in a sample or the upper limit of the assumed concentration range of the target analyte to be measured. Thereby a stoichiometric ratio between first and second capture entity may be achieved. In case the overall number of capture entities is smaller than the number of available epitopes on all target analytes in the sample, a non-stoichiometric binding may occur, or the testing may become insensitive due to the failure to capture essentially all or almost all target analytes in the sample.

In specific scenarios it may not be necessary having an excess amount of capture entities. In such scenarios, it is preferred providing the first and/or the second capture entitiy not in excess of the target analyte. For example, in case of a very high analyte concentration, which is about to approach the number of secondary capture entities, all secondary capture entities on the particles may roughly capture only one target analyte. In this situation the clustering between the detection particles would be no longer problematic or less pronounces. This can, in further specific embodiments, for example be determined by pre-analysing the range of concentration of target analytes in the sample.

In a further specific embodiment of the present invention, a second capture entity as defined herein above may comprise a label as defined herein above. Said label may be bound by a third capture entity on the detection particle as defined herein above. In this specific embodiment, the suitable proportion or amount of the first and/or second capture entities may also be dependent on the amount of the third capture entity, and/or the affinity of said third capture entity. It is, in particular, preferred that situations should be avoided in which the amount of second entity (with the label) is larger than the amount of third entity (on the particle), since then only a portion of the target analyte can be detected. It is therefore preferred that the amount of third capture entities exceeds the amount of second capture entities, e.g. by 10%, 15%, 20%, 25%, 50%, 75%, 100%, 200%, 500%, 1000% or more.

In another example, the suitable proportion or amount of the first and/or second capture entity to be used in a test or other application according to the present invention may depend on the concentration range of the target analyte to be measured. Since the exact concentration of the target molecule would be unknown it is helpful in the context of the present invention to have some assumption on the concentration range of the target analyte in the sample. Such concentration range may be deduced from historic values or previous measurements with similar samples or sample types. Alternatively, the concentration range may be determined on the basis of a pre-test or calibration test, e.g. with a sub-portion of the sample. The assumed concentration range may be a rough estimate of the concentration of the target analyte without control or fine-tuning. The concentration range may be used in order to define the overall number of capture entities to cover all potentially present identical or similar epitopes present in the sample, e.g. by multiplying the upper limit of the assumed concentration with the number of similar or identical epitopes on the target analyte. Thereby a maximum or excess number of capture entities may be determined. Subsequently, the proportion of first to second capture entity may be calculated on the basis of this number and on the basis of the number of identical or similar epitopes per target analyte.

In further alternative embodiments, tests may be conducted simultaneously with different concentrations, for example in different chambers or devices, and then the most appropriate one may be chosen or the target analyte concentration may be determined based on the combined results. For example, the tests may be conducted with different concentrations or amounts of first capture entities, second capture entities and/or third capture entities or binding sites on a detection particle, and/or with different concentrations or amounts of detection particles, and/or with first, second and/or third capture entities with different affinities for the multi-epitope target analyte, e.g. in different chambers or devices, and then the most appropriate concentration or amount of the mentioned elements and the most appropriate combination or proportion of entities may be chosen. This information may subsequently be used for the determination of the target analyte concentration.

In a further specific embodiment, the amount of the first capture entity and the amount of the second capture entity to be used in the context of the present invention may be made dependent on the concentration range of the multi-epitope target analyte to be measured. The concentration range, which may be calculated or deduced as described above, may give an indication with respect to the overall amount of capture entities to be used. The intention behind this embodiment and similar embodiments is to provide a blocking of similar or identical epitopes on the target analyte, which enables to effectively reduce the aggregation of detection particles. Such a blocking may be a significant blocking of similar or identical epitopes on the target analyte, while keeping a small but constant number of the same similar or identical epitopes free of the blocking capture entity (first capture entity) in order to allow a binding of the second capture entity to these epitopes. However, also other possibilities and blocking ratios are envisaged. This may depend on further parameters or factors as defined herein, e.g. the range of concentration of the target analyte.

Thus, the approach may be facilitated if there is at least a rough estimate of the concentration range of the target analyte to be measures since otherwise insufficient numbers of capture entities may be used. It should further be prevented to use too many capture entities in order to save costs and to avoid mutual interactions between first and second capture entities which can jeopardize the accuracy and sensitivity of the underlying tests.

Further, the suitable proportion or amount of the first and/or second capture entity to be used in a test or other application according to the present invention may depend on the affinity of the second and/or the first capture entity. For example, in case the first capture entity (blocking entity) has a lower affinity for the same or identical multiple epitopes of the target analyte than the second capture entity (detection entity), the proportion of said first to said second capture entity should be higher than in the opposite case, where the second capture entity (detection entity) has a lower affinity for the same or identical multiple epitopes of the target analyte than the first capture entity (blocking entity). The affinity of the capture entities may be determined or calculated and entered as factor into an overall calculation with regard to the suitable or optimal proportion of capture entities to be used. Suitable tests have been described herein above. Further suitable tests for determining the affinity of the capture entities would be known to the skilled person, or can be derived from suitable literature sources such as The Immunoassay Handbook, $4^{th}$ Edition, Theory and applications of ligand binding, ELISA and related techniques, D. Wild, Elsevier Science, 2013.

In a further specific embodiment, the amount of the first capture entity to be used in a test or other application according to the present invention may be made dependent on the number of the second capture entity for the multi-epitope target analyte. In this embodiment, the number of the first capture entity may be chosen such that it is present in a higher amount than the second capture entity. This may further made dependent on the amount of potential identical or similar epitopes or binding sites on the target analyte. The proportion of first and second capture entities may follow a corresponding stoichiometry.

In a further specific embodiment, the amount of the second capture entity to be used in the in a test or other application according to the present invention may be made dependent on the number of the first capture entity for the multi-epitope target analyte. In this embodiment, the number of the second capture entity may be chosen such that it is present in a lower amount than the first capture entity. This may further be made dependent on the amount of potential identical or similar epitopes or binding sites on the target analyte. The proportion of first and second capture entities may follow a corresponding stoichiometry.

In case of the presence of a third capture entity on the detection particles, the number of the third capture entity for the labeled second capture entity and/or the affinity of the third capture entity for the labeled second capture entity may be made dependent on the number of first and/or second capture entities, or vice versa, i.e. the number of first and/or second capture entities may be made dependent on the number of third capture entities, in particular on the number of third capture entity on the detection particles. Thus, in a specific embodiment, the amount of the first capture entity and/or the amount of the second capture entity to be used in a test according to the present invention may be made dependent on the number of binding sites on the detection particle for the label. It is preferred that the binding sites are essentially provided by third capture entities as defined herein above. In a further embodiment, the amount of the first capture entity and/or of the second capture entity may be made dependent on: the number of detection particles to be used and the number of the second capture entity for the multi-epitope target analyte.

In a further embodiment, the amount of the first capture entity and/or of the second capture entity may be made dependent on: the number of detection particles to be used; and the number of similar or identical epitopes on the multi-epitope target analyte.

In a further embodiment, the amount of the first capture entity and/or of the second capture entity may be made dependent on: the number of detection particles to be used; and the concentration range of the multi-epitope target analyte to be measured.

In a further embodiment, the amount of the first capture entity and/or of the second capture entity may be made dependent on: the number of detection particles to be used; and the affinity of the first capture entity for the multi-epitope target analyte.

In a further embodiment, the amount of the first capture entity and/or of the second capture entity may be made dependent on: the number of detection particles to be used; and the affinity of the second capture entity for the multi-epitope target analyte.

In a further embodiment, the amount of the first capture entity and/or of the second capture entity may be made dependent on: the number of the second capture entity for the multi-epitope target analyte; and the number of similar or identical epitopes on the multi-epitope target analyte.

In a further embodiment, the amount of the first capture entity and/or of the second capture entity may be made dependent on: the number of the second capture entity for the multi-epitope target analyte; and the concentration range of the multi-epitope target analyte to be measured.

In a further embodiment, the amount of the first capture entity and/or of the second capture entity may be made dependent on: the number of the second capture entity for the multi-epitope target analyte; and the affinity of the first capture entity for the multi-epitope target analyte.

In a further embodiment, the amount of the first capture entity and/or of the second capture entity may be made dependent on: the number of the second capture entity for the multi-epitope target analyte; and the affinity of the second capture entity for the multi-epitope target analyte.

In a further embodiment, the amount of the first capture entity and/or of the second capture entity may be made dependent on the number of similar or identical epitopes on the multi-epitope target analyte; and the concentration range of the multi-epitope target analyte to be measured.

In a further embodiment, the amount of the first capture entity and/or of the second capture entity may be made dependent on: the number of similar or identical epitopes on the multi-epitope target analyte; and the affinity of the first capture entity for the multi-epitope target analyte.

In a further embodiment, the amount of the first capture entity and/or of the second capture entity may be made dependent on: the number of similar or identical epitopes on the multi-epitope target analyte; and the affinity of the second capture entity for the multi-epitope target analyte.

In a further embodiment, the amount of the first capture entity and/or of the second capture entity may be made dependent on the concentration range of the multi-epitope target analyte to be measured; and the affinity of the first capture entity for the multi-epitope target analyte.

In a further embodiment, the amount of the first capture entity and/or of the second capture entity may be made dependent on: the concentration range of the multi-epitope target analyte to be measured; and the affinity of the second capture entity for the multi-epitope target analyte.

In a further embodiment, the amount of the first capture entity and/or of the second capture entity may be made dependent on: the first capture entity for the multi-epitope target analyte; and the affinity of the second capture entity for the multi-epitope target analyte.

In a further embodiment, the amount of the first capture entity and/or of the second capture entity may be made dependent on: the number of detection particles to be used and the number of the second capture entity for the multi-epitope target analyte; and the number of similar or identical epitopes on the multi-epitope target analyte.

In a further embodiment, the amount of the first capture entity and/or of the second capture entity may be made dependent on: the number of detection particles to be used and the number of the second capture entity for the multi-epitope target analyte; and the concentration range of the multi-epitope target analyte to be measured.

In a further embodiment, the amount of the first capture entity and/or of the second capture entity may be made dependent on: the number of detection particles to be used and the number of the second capture entity for the multi-epitope target analyte; and the the affinity of the first capture entity for the multi-epitope target analyte.

In a further embodiment, the amount of the first capture entity and/or of the second capture entity may be made dependent on: the number of detection particles to be used and the number of the second capture entity for the multi-epitope target analyte; and the affinity of the second capture entity for the multi-epitope target analyte.

In a further embodiment, the amount of the first capture entity and/or of the second capture entity may be made dependent on: the number of detection particles to be used and the number of the second capture entity for the multi-epitope target analyte; and the number of similar or identical epitopes on the multi-epitope target analyte and the concentration range of the multi-epitope target analyte to be measured.

In a further embodiment, the amount of the first capture entity and/or of the second capture entity may be made dependent on: the number of detection particles to be used and the number of the second capture entity for the multi-epitope target analyte; and the number of similar or identical epitopes on the multi-epitope target analyte and the affinity of the first capture entity for the multi-epitope target analyte.

In a further embodiment, the amount of the first capture entity and/or of the second capture entity may be made dependent on: the number of detection particles to be used and the number of the second capture entity for the multi-epitope target analyte; and the number of similar or identical epitopes on the multi-epitope target analyte and the affinity of the second capture entity for the multi-epitope target analyte.

In a further embodiment, the amount of the first capture entity and/or of the second capture entity may be made dependent on: the number of detection particles to be used and the number of the second capture entity for the multi-epitope target analyte; and the number of similar or identical epitopes on the multi-epitope target analyte and the concentration range of the multi-epitope target analyte to be measured and the affinity of the first capture entity for the multi-epitope target analyte.

In a further embodiment, the amount of the first capture entity and/or of the second capture entity may be made dependent on: the number of detection particles to be used and the number of the second capture entity for the multi-epitope target analyte; and the number of similar or identical epitopes on the multi-epitope target analyte and the concentration range of the multi-epitope target analyte to be measured and the affinity of the second capture entity for the multi-epitope target analyte.

In a further embodiment, the amount of the first capture entity and/or of the second capture entity may be made dependent on: the number of detection particles to be used and the number of the second capture entity for the multi-epitope target analyte; and the number of similar or identical epitopes on the multi-epitope target analyte and the concentration range of the multi-epitope target analyte to be measured and the affinity of the first capture entity for the multi-epitope target analyte. and the affinity of the second capture entity for the multi-epitope target analyte.

Also envisaged are dependencies of the amount of the first capture entity and/or of the second capture entity on further combinations of any one of the features (i) the number of detection particles to be used;
(ii) the number of the second capture entity for the multi-epitope target analyte;
(iii) the number of similar or identical epitopes on the multi-epitope target analyte;
(iv) the concentration range of the multi-epitope target analyte to be measured;
(v) the affinity of the first capture entity for the multi-epitope target analyte;
(vi) the affinity of the second capture entity for the multi-epitope target analyte,
(vii) the number of the third capture entity for the labeled second capture entity,
and
(viii) the affinity of the third capture entity for the labeled second capture entity; or
(ix) the number of binding sites on the detection particle for the label, e.g. the label present on the second capture entity.

In a particularly preferred embodiment, the proportion of the first to the second capture entity to be used in to be used in a test or other application according to the present invention may be n−1 to 1, with n being the number of identical epitopes on said multi-epitope target analyte. In further embodiments also different proportions are envisaged e.g. n−2 to 1, n−3 to 1, n−4 to 1, n−5 to 1, n−6 to 1 etc. with n being the number of identical epitopes on said multi-epitope target analyte. The proportions may be chosen according to the overall number of identical or similar epitopes on the target analyte, as well as the nature or structure of the target analyte, e.g. in case of similar affinities of the first and second capture entity for the target analyte.

In a specific embodiment of the present invention the time sequence of events during the test, i.e. the sequence of provision of first and/or second capture entity and/or of detection particles may be specified. For example, in one embodiment, first and second capture entity and detection particle may be provided at the same time.

In a further embodiment, the first and the second capture entity may be provided first, i.e. they may be contacted with the target analyte. The detection particle may during this step not be present and be added to the mixture of first and second capture entity and target analyte at a later stage, e.g. after several seconds, or minutes, e.g. 2, 3, 4, 5, 6, 7, 8, 9, 10, 15, 20, 25, 30 min or more after the initial contacting. In this embodiment, the second capture entity is preferably provided with a label as described above. The absence of the detection particle in the first contacting step may avoid a direct interaction between the labeled second capture entity and the detection particle, since both, i.e. the second capture entity with the label and the detection particle may interact. By temporarily separating both, it is possible to achieve a proportional binding of first and second capture entities to the target analyte without interference from the detection particle. In a further embodiment, the first capture entity may be provided first, while the second capture entity and the detection particle may be provided later on, e.g. after several seconds, or minutes, e.g. 2, 3, 4, 5, 6, 7, 8, 9, 10, 15, 20, 25, 30 min or more after the initial contacting.

In yet another embodiment, the first capture entity and the detection particle may be provided first, while the second capture entity may be provided later on, e.g. after several seconds, or minutes, e.g. 2, 3, 4, 5, 6, 7, 8, 9, 10, 15, 20, 25, 30 min or more after the initial contacting.

In a further aspect the present invention relates to a method for the detection of a multi-epitope target analyte as defined herein above in a sample and/or for the determination of the concentration of said multi-epitope target analyte in a sample, comprising the steps of:

applying a first capture entity as defined herein above which can specifically bind to at least one epitope on said multi-epitope analyte, characterized in that said first capture entity blocks the at least one epitope from binding to a detection particle;

applying a second capture entity as defined herein above, which can specifically bind to the same epitope of said multi-epitope target analyte as the first capture entity, wherein the second capture entity comprises a label permitting the binding of second capture entity to said detection particle, as described above or wherein the second capture entity is present on said detection particle as described above; and detecting said multi-epitope target analyte with a detection particle as defined herein above, being capable of binding to said label present on said second capture entity, or with a detection particle comprising a second capture entity which can specifically bind to said epitope of said multi-epitope target analyte, wherein said detection particles are prevented from aggregating.

The method may be carried out under observation of the definitions for the amount and/or proportion of the first and second capture entity as provided herein above.

Furthermore, the method may be carried out on the basis of different time sequences as outlined above. For example, in one embodiment, first and second capture entity and detection particle may be provided at the same time during the method.

In a further embodiment, the first and the second capture entity may be provided first during the method, i.e. they may be contacted with the target analyte. The detection particle may during this step not be present and be added to the mixture of first and second capture entity and target analyte at a later stage, e.g. after several seconds, or minutes, e.g. 2, 3, 4, 5, 6, 7, 8, 9, 10, 15, 20, 25, 30 min or more after the initial contacting step of the method. In this embodiment, the second capture entity is preferably provided with a label as described above. The absence of the detection particle in the first contacting step during the method may avoid a direct interaction between the labeled second capture entity and the detection particle, since both, i.e. the second capture entity with the label and the detection particle may interact. By temporarily separating both during the method, it is possible to achieve a proportional binding of first and second capture entities to the target analyte without interference from the detection particle.

In a further embodiment, the first capture entity may be provided first during the method, while the second capture entity and the detection particle may be provided later on, e.g. after several seconds, or minutes, e.g. 2, 3, 4, 5, 6, 7, 8, 9, 10, 15, 20, 25, 30 min or more after the initial contacting.

In yet another embodiment, the first capture entity and the detection particle may be provided first during the method, while the second capture entity may be provided later on, e.g. after several seconds, or minutes, e.g. 2, 3, 4, 5, 6, 7, 8, 9, 10, 15, 20, 25, 30 min or more after the initial contacting.

The detection step may further be combined with any kind of suitable readout method, e.g. the amount of detection particles may be determined with any suitable optical or magnetic methodology.

As outlined above, it is essential to the above described method that during the detection of a multi-epitope target the aggregation of the detection particle is prevented. This due to the molecular structure and form of the particles involved (see, for example, the illustration of FIG. 6).

Also envisaged are assay or method formats based on competitive approaches, which typically require the presence of a competitor or a target analog. The term "target analog molecule" as used herein refers to any molecule, which competes with the target analyte for the binding to the first or second capture entity as defined herein. In such a case the target analyte may interfere with the binding of the first or second capture entity to the target analog molecule.

Envisaged by the present invention are also competition or inhibition assay or method formats, where the first or second capture entity may bind a target analog molecule attached on a sensor surface. This binding can be prevented if a target analyte as described herein is present in the sample and if this target analyte binds to the first or second capture entity first. For example, a small drug molecule can be detected using the envisaged method if an analog of the drug molecule is e.g. immobilized to a flat sensor surface. If no drug molecule is present in the sample, all particles with the capture entity recognizing the target analyte may bind to the target analog molecule on the sensor surface. However, in the presence of drug (target) analytes, which interfere with this binding, the anti-drug capture entities cannot bind or bind less to the target analog on the sensor surface. In such a case the amount of particles on the sensor surface is inversely related to the amount of target analytes.

In particularly preferred embodiment, the detection step of a method as defined herein above, i.e. the detection of said multi-epitope target analyte in a sample and/or the determination of the concentration of said multi-epitope target analyte in a sample as defined herein above may be performed in a suitable system. The system may, for example, be adapted to the detection of a detection particle as described herein. For example, the system may be adapted to allow or perform the following steps:

binding of the multi-epitope target analyte to the detection particle as described herein above, i.e. via the second capture entity as define herein, contacting the detection particle bound to the multi-epitope target analyte with a sensor surface of the system;

allowing for the binding of a different (non-identical or not similar) epitope of the multi-epitope target analyte by a third capture entity being present on said sensor surface of the system; and detecting the particles remaining at said sensor surface.

In one embodiment, the present invention also envisages the provision of a system as defined herein, e.g. a biosensor system. Such a biosensor systems may comprise, for example, a biosensor cartridge comprising a sample container, a sensor device for sensing particles, a detection system, and optionally a magnetic field generator. The systems may, in further embodiments, comprise one or more additional functional units such as a readout system, e.g. a screen or printer, an interface for database or computer systems, a calibration unit, a direct or indirect connectivity with high-throughput devices etc. Particularly envisaged by the present invention are handheld devices for quick and instant analysis where a cartridge including the assay format or ingredients necessary for carrying out the methods according to the present invention may be inserted. Typically, such a device comprises a power supply, preferably in form of rechargeable batteries, a display, wireless connectivity such as WLAN for quick database access, or access to a laboratory information system.

The "sensor surface" may be a flat surface which is capable of interacting with the detection particle. The sensor surface may typically be functionalized with capture entities or other functional elements such as target analogs, e.g. in the case of an inhibition assay or corresponding method. The term "interacting" as used herein means that the detection particle may be bound, preferably reversibly bound, to the surface. The sensor surface may further be connected with downstream electronic or optical or magnetic etc. devices allowing to perform additional activities on the detection particle.

The term "different epitope" as used herein refers to an epitope which is not identical and not similar to the multiple epitopes on the target analyte as described above. The epitope may essentially not be recognized or essentially not be bound by the first or second capture entity as described above. There may further essentially be no cross-reactivity between said first or second capture entity and the different (non-identical or not similar) epitope as described above. This extra epitope or binding site may additionally be present on the multi epitope target analyte. However, this epitope may be present only once or two times, i.e. it may not qualify as multiple epitope according to the definitions provided above. In specific embodiments, the epitope may also be present in a higher number, i.e. it may also be provided as multi-epitope, with three or more identical or similar copies on the target analyte, wherein however these copies are not identical or similar to the epitopes to which the first and second capture analyte can bind.

It is preferable that the different epitope as defined above can be recognized and bound by a third capture entity. The third capture entity may preferably be present on the sensor surface or on a detection surface or the like. The third capture entity may be composed of or comprise the same material as the first and second capture entity, e.g. an antibody, fragment thereof, DNA, RNA, non-immunoglobulin protein etc. as defined herein above. It is preferred that the third capture entity is monoclonal antibody immobilized on the sensor surface. An illustrative, but not limiting, example of how such an interaction at the sensor surface may be performed is provided in FIG. 6. Here the target analyte is directly bound to the sensor surface via the third capture entity present on the sensor surface.

In a further specific embodiment, the binding to the sensor surface may also be performed via an interaction between a third capture entity on the sensor surface and a cognate epitope or label on the detection particle, which only becomes accessible in case the target analyte has been bound to the detection particle. For example, the capture entity on the the sensor surface, e.g. an antibody, may recognize the interface between the capture entity, on the particle, e.g. antibody, and the target analyte. The interface may correspond to a new epitope that only become available when the target analyte is bound.

The detection of the target analyte (via the detection particle) may finally be based on a detection of complexes which remain at the sensor surface. This may include previous activities to "clean" the sensor surface in order to get rid of non-specifically bound detection particles. Such an activity may comprise any removing activity for the detection particles conceivable to a skilled person. It is preferred that said removing activity is a magnetic actuation of the detection particle, which is a magnetic particle as defined herein above.

Particularly envisaged by the present invention is the specific use of magnetic particles as defined herein above, which can be actuated by applying a magnetic field such that the analytical procedure can be accelerated. It is also envisaged by the present invention that the use of a magnetic field may reduce the background signal due to removal of unspecifically bound particles. An exemplary optomagnetic system suitable for the method of detection according to the present invention is depicted in FIG. 1. Thus, a method according to the present invention also comprises the additional step of magnetically actuating the magnetic detection particles as defined herein above before the detection.

In one embodiment of the present invention a magnetic force is applied to bring the particles into close proximity with the sensor surface.

In another preferred embodiment of the present invention the detection of bound particles, e.g. magnetic particles, occurs via frustrated total internal reflection (FTIR) or via measurement of scattered light from said bound particles near the surface or via the optical detection of cluster formation. Particularly preferred are sensing devices based on an optical detection of particles, especially magnetic particles as defined herein above. Corresponding details may be derived from the exemplary device illustrated in FIG. 1, which comprises a light source and a light detection system, and constitutes a specific embodiment according to the present invention. The optical methods used for detection typically measure a change in light signal, i.e. a difference in light reflected from the magnetic particles and which can be detected by optical means.

For instance, such methods may include techniques such as the detection of scattered light or detection based on total internal reflection (TIR) or frustrated total internal reflection (FTIR). Preferably, the change in light signal refers to only those magnetic particles being bound by virtue of the binding of the third capture entity to the sensor surface. Details would be known to the person skilled in the art, or can be derived from suitable references, such as Bruls et al., Lab Chip, 2009, 9. 2504-3510.

As used herein the term "total internal reflection" describes a condition present in certain materials when light enters one material from another material with a higher refractive index at an angle of incidence greater than a specific angle. The specific angle at which this occurs depends on the refractive indices of both materials, also referred to as critical angle and can be calculated mathematically (Snell's law, law of refraction). In absence of particles, e.g. magnetic particles, no refraction occurs and the light beam from the light source is totally reflected. If a particle, e.g. magnetic particle, is close to the surface or is in contact with the sensor surface the light rays are said to be frustrated by the particle and reflection at that point is no longer total. The signal, which may be defined as the decrease of the totally internal reflected signal can be calculated.

The signal is more or less linearly dependent on the concentration of particles on the surface (surface density n). The signal can be expressed as:

$$S=\beta \tilde{n}$$

wherein S is the measured signal change in % and β is a conversion factor from surface density to signal change.

In a preferred embodiment of the present invention detection of bound particles, e.g. magnetic particles, occurs via frustrated total internal reflection (FTIR) or via measurement of scattered light from said bound particles near the surface.

The detection may, in a particularly preferred embodiment be carried out in an optomagnetic system, wherein said particles is are magnetic particles which are magnetically actuated and optically detected in a stationary sample fluid.

In a further aspect the present invention relates to the use of a first capture entity as defined herein above which specifically bind to at least one epitope on a multi-epitope analyte comprising to or more similar or identical epitopes for the blocking of the at least one epitope. The blocking may in particular be a blocking from a binding of the target analyte to a detection particle as defined herein. The particle may preferably be a magnetic particle as defined herein. The magnetic particle may further be preferably used in an optomagnetic system as defined herein. The blocking may, in alternative embodiments, also be a blocking from a binding to any other particle or interacting entity.

In particularly preferred embodiments of the present invention the multi epitope target analyte to be detected or measured is a target comprising at least 3 or more similar or identical epitopes. The most preferred target analytes are CRP and D-dimer. Further target analytes with two or more similar or identical epitopes are also encompassed within the scope of the present invention.

In a further group of embodiments the present invention relates to a kit of parts comprising at least a first capture entity which can specifically bind to at least one epitope on said multi-epitope analyte, preferably as defined herein above. In a specific embodiment, the kit of parts comprises one capture entity which can specifically bind to at least one epitope on said multi-epitope analyte, preferably as defined herein above. In a further specific embodiment, the kit of parts comprises a first capture entity which can specifically bind to at least one epitope on said multi-epitope analyte, preferably as defined herein above; and a second capture entity, which can specifically bind to the same epitope of said multi-epitope target analyte as the first capture entity, preferably as defined herein above.

Said first capture entity which can specifically bind to at least one epitope on said multi-epitope analyte may, in certain embodiments, be capable of blocking the at least one epitope from binding to a detection particle. Said second capture entity may, in certain embodiments, comprise a label permitting the binding of second capture entity to a detection particle. In further specific embodiments, the kit of parts may further comprise a third capture entity, which is preferably a monoclonal antibody immobilized on a surface, e.g. a sensor surface. Accordingly, the kit of parts may be provided in the form of or be based on a surface, e.g. a sensor surface. The sensor may be considered as part of the kit in certain embodiments, or as external element, which may be used together with the kit.

In further embodiments, the kit of parts may optionally or additionally comprise a detection particle, i.e. a particle comprising or consists of any suitable material known to the person skilled in the art, e.g. the detection particle may comprise, or consist of, or essentially consist of inorganic or organic material, more preferably be a magnetic particle as defined herein above.

In specific embodiments, the kit of parts according to the present invention may comprise as capture entities an antibody, fragment thereof, DNA, RNA, non-immunoglobulin protein etc. as defined herein above.

Typically, a kit according to the invention may comprise accessory ingredients such a buffers, blocking reagents, ions, e.g. bivalent cations or monovalent cations, calibration proteins, secondary antibodies, detection reagent such as detection dyes and any other suitable compound or liquid necessary for the performance of a protein detection based known to the person skilled in the art. Such ingredients are known to the person skilled in the art and may vary depending on the detection method carried out. Additionally, the kit may comprise an instruction leaflet and/or may provide information as to the relevance of the obtained results.

In a further group of embodiments the present invention relates to a cartridge comprising at least a first capture entity which can specifically bind to at least one epitope on said multi-epitope analyte, preferably as defined herein above. In a specific embodiment, the cartridge comprises one capture entity which can specifically bind to at least one epitope on said multi-epitope analyte, preferably as defined herein above. In a further specific embodiment, the cartridge comprises a first capture entity which can specifically bind to at least one epitope on said multi-epitope analyte, preferably as defined herein above; and a second capture entity, which can specifically bind to the same epitope of said multi-epitope target analyte as the first capture entity, preferably as defined herein above.

In further specific embodiments, the cartridge may further comprise a third capture entity, which is preferably a monoclonal antibody.

In further specific embodiments, the cartridge may comprise as capture entities an antibody, fragment thereof, DNA, RNA, non-immunoglobulin protein etc. as defined herein above.

A "cartridge" as used herein refers to a container like structure made from any suitable material like glass, any transparent plastic, or a semiconductor in which the sample is measured. In specific embodiments, the cartridge may comprise a single container or chamber which comprises capture entities etc. as defined herein above. In alternative embodiments, the cartridge may comprise more than one container or chamber which comprises capture entities etc. as defined herein above, e.g. 2, 3, 4, 5 or more different chambers or containers. These chambers or container are preferably in fluid connection with each other, or with a rinsing or fluidic transportation system. Capture entities and detection particles according to the present invention may preferably be provided similarly in all chambers. In optional embodiments, certain chambers may comprise only a subset of the Capture entities and detection particles or a lower or higher amount in comparison to the other chambers.

Particles, e.g. magnetic particles as described herein may be already present in the cartridge, e.g. in one or more than one chamber, when a sample is introduced, be introduced together with the sample, or be introduced after the sample has been injected into the sample container. The cartridge may further comprise a sensor surface, e.g. as defined herein above. Preferably, the sensor surface is located at the bottom of the cartridge. The cartridge may, in specific embodiments, be provided as exchangeable entity, e.g. in a standalone component separate from the sensor device. Due to possible contamination with a sample, the cartridge may preferably be a disposable item, made for instance from plastics by injection molding. Also envisaged are recyclable cartridges or recyclable cartridge parts, e.g. cartridges or cartridge parts, which can be cleansed or sterilized.

The following figures are provided for illustrative purposes. It is thus understood that the figures are not to be construed as limiting. The skilled person in the art will clearly be able to envisage further modifications of the principles laid out herein.

The invention claimed is:

1. A method for preventing aggregation of detection particles in a test for detecting a multi-epitope target analyte comprising two or more similar or identical epitopes in a sample and/or for determining a concentration of said multi-epitope target analyte in the sample, the method comprising the steps of:
providing a detection particle;
applying a blocking entity to the sample, the blocking entity configured to specifically bind to at least one epitope on said multi-epitope target analyte and block the at least one epitope from binding to the detection particle, the applying of the blocking entity to the sample including covering a majority of similar or identical epitopes on the multi-epitope target analyte with the blocking entity and leaving only less than the majority of the similar or identical epitopes on the multi-epitope target analyte unblocked; and
applying a capture entity to the sample, the capture entity configured to specifically bind to a same or a similar epitope of said multi-epitope target analyte as the blocking entity, the capture entity being capable of interacting with the detection particle, wherein said detection particle is a magnetic particle; and
wherein said magnetic particle is actuated by coils in a pulsed manner.

2. The method of claim 1, wherein the capture entity comprises a label permitting binding of the capture entity to said detection particle.

3. The method of claim 1, wherein said capture entity is present on said detection particle.

4. A method for detection of a multi-epitope target analyte in a sample and/or for determination of a concentration of said multi-epitope target analyte in the sample, comprising the steps of:
applying a non-labeled first capture entity to the sample, which can specifically bind to at least one epitope on said multi-epitope target analyte, wherein said first capture entity blocks the at least one epitope from binding to a detection particle, wherein applying the first capture entity leads to the covering of a majority of similar or identical epitopes on the multi-epitope target analyte and leaving only a small portion of single epitopes left;
applying a second capture entity to the sample, which can specifically bind to a same epitope of said multi-epitope target analyte as the first capture entity, wherein the second capture entity comprises a label permitting the binding of the second capture entity to said detection particle; and
detecting said multi-epitope target analyte with the detection particle, wherein the detection particle is capable of binding to said label present on said second capture entity,
wherein said detection particles are prevented from aggregating.

5. The method of claim 1, wherein an amount of said blocking entity and/or an amount of said capture entity to be used in said test is made dependent on:
(i) a number of detection particles to be used;
(ii) a number of the capture entity for the multi-epitope target analyte;
(iii) a number of similar or identical epitopes on the multi-epitope target analyte;
(iv) a concentration range of the multi-epitope target analyte to be measured;
(v) an affinity of the blocking entity for the multi-epitope target analyte;
(vi) an affinity of the capture entity for the multi-epitope target analyte; and/or
(vii) a number of binding sites on the detection particle for a label.

6. The method of claim 5, wherein a proportion of the blocking entity to the capture entity to be used in said test for detecting the multi-epitope target analyte in the sample and/or for determining the concentration of said multi-epitope target analyte in the sample is n−1 to 1, with n being a number of identical epitopes on said multi-epitope target analyte.

7. The method of claim 1, wherein said sample comprising said multi-epitope target analyte is contacted with said blocking entity and/or said capture entity before said detection particle is added.

8. The method of claim 1, wherein said blocking entity and/or said capture entity is an antibody, an antibody fragment, a DNA molecule, an RNA molecule, or a non-immunoglobulin protein.

9. The method of claim 8, wherein said non-immunoglobulin protein is a designed ankyrin-repeat protein (DARPin), affibody molecule, adnectin, anticalin, affilin, avimer, knottin, fynomer, phylomer, or kunitz domain peptide.

10. The method of claim 1, wherein said detection of said multi-epitope target analyte in the sample and/or said determination of the concentration of said multi-epitope target analyte in the sample is performed in a system comprising the steps of:
binding said multi-epitope target analyte to said detection particle,
contacting the detection particle bound to the multi-epitope target analyte with a sensor surface of the system;
allowing for the binding of a different (non-identical or not similar) epitope of the multi-epitope target analyte by another capture entity being present on said sensor surface of the system; and
detecting particles remaining at said sensor surface.

11. The method of claim 10, wherein said detection of the multi-epitope target analyte in the sample and/or said determination of the concentration of said multi-epitope target analyte in the sample is performed in an optomagnetic system, and wherein optical detection is in a stationary sample fluid.

12. The method of claim 11, additionally comprising the step of magnetically actuating magnetic particles before detection.

13. The method of claim 4, wherein only single epitopes are left.

14. The method of claim 1, wherein the blocking entity and the capture entity are applied to the sample in excess of an estimated total number epitopes within the sample.

15. The method of claim 1, wherein the detection particle is added after the blocking entity and the capture entity are applied to the sample.

16. The method of claim 1, wherein the capture entity and the detection particle are added to the sample a predetermined amount of time after the blocking entity is applied.

17. The method of claim 16, wherein the predetermined amount of time is one minute or greater.

* * * * *